United States Patent
Li

(10) Patent No.: US 10,116,203 B2
(45) Date of Patent: Oct. 30, 2018

(54) TRANSFORMER INCLUDING A CURRENT INDUCTION DEVICE HAVING AN AMPLIFIER CIRCUIT

(71) Applicant: Xi'an TuoFeng Electromechanical Co., Ltd., Xi'an OT (CN)

(72) Inventor: Huipeng Li, Xi'An (CN)

(73) Assignee: Xi'an TuoFeng Electromechanical Co., Ltd., Xi'an (CN)

( * ) Notice: Subject to any disclaimer, the term of this patent is extended or adjusted under 35 U.S.C. 154(b) by 0 days.

(21) Appl. No.: 15/414,849

(22) Filed: Jan. 25, 2017

(65) Prior Publication Data

US 2018/0152096 A1    May 31, 2018

(30) Foreign Application Priority Data

Nov. 30, 2016  (CN) .......................... 2016 1 1081043

(51) Int. Cl.
| | |
|---|---|
| *H02M 7/217* | (2006.01) |
| *H01F 38/30* | (2006.01) |
| *H03F 3/21* | (2006.01) |
| *H02M 1/32* | (2007.01) |
| *G01N 33/00* | (2006.01) |

(52) U.S. Cl.
CPC .......... *H02M 1/32* (2013.01); *G01N 33/0036* (2013.01); *H01F 38/30* (2013.01); *H02M 7/217* (2013.01); *H03F 3/21* (2013.01)

(58) Field of Classification Search
CPC .... H02M 1/32; H02M 7/217; G01N 33/0036; H01F 38/30; H03F 3/21
See application file for complete search history.

(56) References Cited

U.S. PATENT DOCUMENTS

| | | | | | |
|---|---|---|---|---|---|
| 4,058,758 | A | * | 11/1977 | Peterson ............. | H02H 7/1213 363/21.08 |
| 4,222,099 | A | * | 9/1980 | Hill ........................ | H02M 7/06 340/646 |
| 4,356,371 | A | * | 10/1982 | Kiuchi .................. | H05B 6/062 219/626 |
| 4,937,727 | A | * | 6/1990 | Leonardi ........... | H02M 3/33523 363/19 |
| 5,903,183 | A | * | 5/1999 | Inukai ................ | G03G 15/1675 327/540 |

(Continued)

*Primary Examiner* — Jeffrey Gblende
*Assistant Examiner* — David A. Singh
(74) *Attorney, Agent, or Firm* — Sand & Sebolt

(57) ABSTRACT

A highly stable transformer, including a first transformer, a second transformer and a current induction device. The current induction device is provided in a load line of the first transformer for detecting an induction current in the load line of the first transformer. An induction load terminal of the current induction device is connected to a control winding. The control winding is provided in a winding of the second transformer to generate an induction voltage in the winding according to the induction current value and output a voltage value matching the load. The transformer has a zero voltage deviation, can be applied to precise appliance circuits and will not produce voltage drop. The transformer adopts active loaded lines, has good operation efficiency and good stability, saves main capacitor loss of no-load and unequal loads, and improves the startup performance of the transformer to any corresponding loads in a full-load condition.

12 Claims, 1 Drawing Sheet

(56) References Cited

U.S. PATENT DOCUMENTS

| | | | | |
|---|---|---|---|---|
| 6,473,317 B1* | 10/2002 | Simopoulos | ...... | H02M 3/33592 363/21.06 |
| 2006/0152947 A1* | 7/2006 | Baker | ................. | H02M 1/4241 363/16 |
| 2007/0097715 A1* | 5/2007 | Choi | ...................... | H02M 3/28 363/24 |
| 2010/0026208 A1* | 2/2010 | Shteynberg | ........ | H05B 33/0815 315/297 |
| 2012/0314456 A1* | 12/2012 | Lanni | ................. | H02M 1/4258 363/21.02 |
| 2015/0055379 A1* | 2/2015 | Fang | ...................... | H02M 1/34 363/21.17 |

* cited by examiner

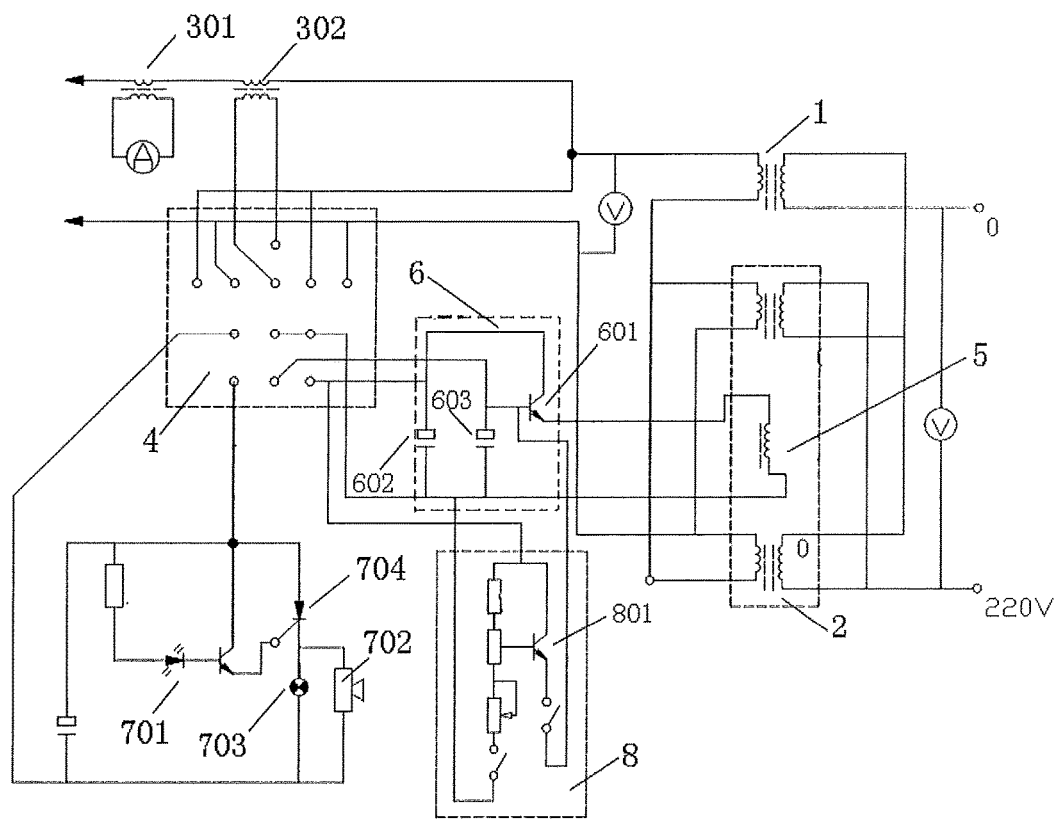

TRANSFORMER INCLUDING A CURRENT INDUCTION DEVICE HAVING AN AMPLIFIER CIRCUIT

TECHNICAL FIELD

The present invention relates to the field of basic electric elements and in particular to a highly stable transformer.

BACKGROUND

Special equipment has problems of severe power idle loss, heavy load, and unstable load size during operation. Conventionally, those skilled in the art seek to reduce idle loss by adjusting the power input circuit to solve the above problems. However, such adjustment is cumbersome and has poor safety and stability.

SUMMARY

In view of the above defects and problems of the prior art, an object of the embodiments of the present invention is to provide a highly stable transformer.

In order to realize the above object, the present invention provides a highly stable transformer, including a first transformer, a second transformer and a current induction device. The current induction device is provided in a load line of the first transformer and detects an induction current in the load line of the first transformer. The induction output end of the current induction device is connected to a control winding. The control winding is provided in a winding of the second transformer for generating an induction voltage in the winding of the second transformer to cause the second transformer to supplement the output power of the first transformer.

The primary coil of the first transformer is connected to the primary coil of the second transformer in series and the secondary coil of the first transformer is connected to the secondary coil of the second transformer in series.

The highly stable transformer may further include a three-terminal synchronization rectifier provided in an induction output line of the current induction device.

The highly stable transformer may further include an amplifier circuit provided in the induction output line of the current induction device.

The amplifier circuit protects a first amplifier circuit and a second amplifier circuit, the first amplifier circuit having a first amplification coefficient value and the second amplifier circuit having a second amplification coefficient value.

The highly stable transformer may further include a humidity sensor and an amplification switching adjustment controller. The humidity sensor is provided in the load line and detects an environment humidity value of the load line. An induction output end of the humidity sensor is connected to the input end of the amplification switching adjustment controller, and the output end of the amplification switching adjustment controller is connected to the first amplifier circuit and the second amplifier circuit for making a switch from the first amplifier circuit to the second amplifier circuit if the environment humidity value exceeds a preset value.

The highly stable transformer may further include an over-range adjustment circuit connected to the amplifier circuit and adjusting the amplification multiple of the amplifier circuit.

The highly stable transformer may further include an alarm unit connected to the three-terminal synchronization rectifier and driving the alai'u unit to generate an alarm if an induction value output by the current induction device exceeds a preset value.

The highly stable transformer may further include a control winding current induction device, a standby controller and a standby control winding. The control winding current induction device is provided in the circuit of the control winding and detects an induction current value of the control winding. The input end of the standby controller is connected to the output end of the current induction device and the output end of the control winding current induction device respectively. The output end of the standby controller is connected to the standby control winding. The standby control winding is started up to operate when it is detected that the induction current in the load line and the current value of the control winding have a match value which is not within a preset match interval. The standby control winding is provided in the winding of the second transformer.

The highly stable transformer may further include a control winding cutoff switch provided in the control winding line, connected to the output end of the standby controller and being cut off when the standby controller drives the standby control winding to start up.

The present invention has the following beneficial effects. The transformer according to the present invention has obvious energy-saving effects; the voltage deviation is 0; and it can be applied to precise appliance circuits and will not produce voltage drop. The transformer adopts active loaded lines, has good operation efficiency and good stability, greatly saves main capacitor loss of no-load and unequal loads, and improves the startup performance of the transformer to any corresponding loads in a full-load condition.

BRIEF DESCRIPTION OF THE DRAWINGS

In order to illustrate the technical solution in the embodiments of the present invention or in the prior art more clearly, the drawings to be used in the description of the embodiments or the prior art will be introduced briefly herein below. Apparently, the drawings are merely some embodiments of the present invention. For a person skilled in the art, other drawings may be obtained according to these drawings without any inventive efforts.

FIG. 1 is a schematic diagram of circuit connections according to an embodiment of the present invention.

DETAILED DESCRIPTION

Hereinafter, the technical solution of the present invention will be described clearly and completely in conjunction with the embodiments of the present invention. Obviously, the described embodiments are merely some embodiments of the present invention. Other embodiments obtained by those skilled in the art according to the embodiments of the present invention without any inventive efforts shall fall within the scope of protection of the present invention.

As shown in FIG. 1, the highly stable transformer according to the present invention includes a first transformer 1 and a second transformer 2. The primary coil of the first transformer 1 is connected to the primary coil of the second transformer 2 in series and the secondary coil of the first transformer 1 is connected to the secondary coil of the second transformer 2 in series. A current induction device is provided in a load line of the first transformer and includes a current induction transformer 302 and an output ampere meter 301. The current induction transformer 302 detects an induction current in the load line of the first transformer 1.

The induction output end of the current induction device is connected to a control winding 5. The control winding 5 is provided in a winding of the second transformer 2 for generating an induction voltage in the winding of the second transformer 2 to cause the second transformer 2 to supplement the output power of the first transformer 1. The highly stable transformer may further include a three-terminal synchronization rectifier 4 provided in an induction output line of the current induction device. The current induction transformer 302 is connected into the three-terminal synchronization rectifier 4 and the three-terminal synchronization rectifier 4 is connected out to the control winding 5. The highly stable transformer may further include an amplifier circuit 6. A ground capacitor is provided at the base of a triode 601. The triode may use 3DD15. The ground capacitor includes a first capacitor 602 and a second capacitor 603. The nominal operation voltage of the first capacitor is 100V and the nominal capacity is 47 µf. The nominal operation voltage of the second capacitor is 50V and the nominal capacity is 0.1 µf. The amplifier circuit 6 is provided in the induction output line of the current induction device. The amplifier circuit comprises a first amplifier circuit and a second amplifier circuit. The first amplifier circuit has a first amplification coefficient value and the second amplifier circuit has a second amplification coefficient value.

The highly stable transformer may further include a humidity sensor and an amplification switching adjustment controller. The humidity sensor is provided in the load line and detects an environment humidity value of the load line. The induction output end of the humidity sensor is connected to the input end of the amplification switching adjustment controller, and the output end of the amplification switching adjustment controller is connected to the first amplifier circuit and the second amplifier circuit for making a switch from the first amplifier circuit to the second amplifier circuit if the environment humidity value exceeds a preset value.

The highly stable transformer may further include an over-range adjustment circuit 8 connected to the amplifier circuit 6 for adjusting the amplification multiple of the amplifier circuit. A triode 801 in the over-range adjustment circuit 8 may use 3DG12. The highly stable transformer may further include an alarm unit connected to the three-terminal synchronization rectifier 4 and generating an alarm if an induction value output by the current induction device exceeds a preset value. The alarm unit includes a photosensitive tube 701, a silicon controlled rectifier 704, a failure display lamp 703 and a buzzer 702. The model of the photosensitive tube 701 is 3DJ12. If the induction value is greater than a preset value, then the failure display lamp and the buzzer generate an alarm.

The highly stable transformer may further include a control winding current induction device, a standby controller and a standby control winding. The control winding current induction device is provided in the circuit of the control winding and detects an induction current value of the control winding. The input end of the standby controller is connected to the output end of the current induction device and the output end of the control winding current induction device respectively, and the output end of the standby controller is connected to the standby control winding. The standby control winding is activated to operate when it is detected that the induction current in the load line and the current value of the control winding have a matching value out of a preset matching interval. The standby control winding is provided in the winding of the second transformer.

The highly stable transformer may further include a control winding cutoff switch provided in the control winding line and connected to the output end of the standby controller. The switch can be cut off when the standby controller drives the standby control winding to start up.

When power is supplied initially, the first transformer and the second transformer are connected in series to share half voltage as an idle load and the output end supplies power to the amplifier through the three-terminal synchronization rectifier so that the control winding of the transformer is in a state ready for power on. The current induction transformer at the output end sends a synchronization signal to the three-terminal synchronization rectifier and is in a state ready for power on. The output ampere meter is in a state ready for power on. The main transformer loses balance instantly upon loading, the output end of the transformer sends signals representing the unbalance to the three-terminal synchronization rectifier. The amplifier circuit is ready for power on. A power signal inducted by the current induction transformer enters a DC amplifier after being rectified and then the amplified signal directly drives the control winding of the transformer to balance the transformation difference of the two transformers and thus stabilize the required real-time output power. The input power is also adjusted correspondingly. This transformer is developed for solving the problem that special equipment has severe power idle loss, which can solve the problems that special equipment has heavy startup load and the load varies during operation. By using the transformer, the idle loss value under small load can be reduced, and no voltage drop will occur when a heavy load is applied. Thus the following advantages can be realized: a distinct energy-saving effect is available. For example, when a 500 W transformer uses 100 W power, the total input power contains the idle loss of the current transformer and 100 W transformer loss plus 100 W load value. The voltage deviation is 0. Thus, the present invention can be applied to precise appliance circuits. There is no voltage drop, for example, this transformer may start up a 500 W motor and, under certain extreme conditions, may also start up a 2-3 KW motor.

By adopting two transformers with different windings driven by parallel lines, the present invention realizes mutual resistance balance and thus input and output impedance balance, divides the idle loss power evenly and reduces power consumption. When power is initially supplied, the first transformer and the second transformer are connected in series to respectively share the load so that each has a relatively small load, and the output end thereof supplies power to the DC amplifier through the synchronization rectifier so that the control winding of the transformer is in a state ready for power on. Another current induction transformer at the output end sends a synchronization signal to the synchronization rectifier and is ready for power on. The ampere meter and transformer are also ready for power on. Safety lines may comprise high pulse alarming and X light interference alarming being in a standby state which can start up automatically if there are high pulses or X light interferences. The power conversion transformer mainly comprises two transformers with different windings and adopts balanced lines to drive the mutual resistance between the two transformers to be balanced and realize equilibrium of input and output impedances and thus realize the object of stabilized voltage output. In the case where the mutual resistance between the two transformers reaches balance, the idle loss power is divided by the two transformers evenly and thus the idle loss is insignificant. When applying or increasing a load, the two transformers induct mutually to form load-level power consumption and effective operation power. Thus, automatic power conversion performance is achieved and a match between the input power and the output power can be obtained. The output of the transformer is a voltage transformation difference which occurs when the balance point of the two transformers shifts. Thus, the above circuit functions as the power supply circuit of the main output power. In this circuit, mutual induction is formed in an active loaded line.

Taking 500 W power as an example of basis for parameter designing, the parameters of the circuit according to an embodiment of the present invention are: 220V/500W, 17.6W/80mA for idle loss, and the full-load output is 16V, 28A/440W. The idle loss limitation data is 220V/500W, 4.96W/68mA.

The foregoing is merely particular embodiments of the present invention. However, the protection scope of the present invention is not limited to this. Any variations or replacements readily contemplated to those skilled in the art without departing the scope of the present invention shall be covered in the protection scope of the present invention. Thus, the protection scope of the present invention shall be based on the claims.

What is claimed is:

1. A transformer comprising:
a first transformer;
a second transformer;
a current induction device; and
an amplifier circuit, wherein the current induction device is provided in a load line of the first transformer for detecting an induction current in the load line of the first transformer; wherein an induction output end of the current induction device is connected to a control winding; and the control winding is provided in a winding of the second transformer for generating an induction voltage in the winding of the second transformer so as to supplement the output power of the first transformer;
wherein the amplifier circuit is provided in an induction output line of the current induction device, wherein the amplifier circuit protects a first amplifier circuit and a second amplifier circuit, the first amplifier circuit having a first amplification coefficient value and the second amplifier circuit having a second amplification coefficient value;
wherein a primary coil of the first transformer is connected to a primary coil of the second transformer in series and a secondary coil of the first transformer is connected to a secondary coil of the second transformer in series; and
wherein a three-terminal synchronization rectifier is provided in the induction output line of the current induction device.

2. The transformer according to claim 1, further comprising a humidity sensor and an amplification switching adjustment controller, the humidity sensor being provided in the load line for detecting an environment humidity value of the load line, the induction output end thereof being connected to the input end of the amplification switching adjustment controller, and the output end of the amplification switching adjustment controller being connected to the first amplifier circuit and the second amplifier circuit for making a switch from the first amplifier circuit to the second amplifier circuit if the environment humidity value exceeds a preset value.

3. The transformer according to claim 1, further comprising an over-range adjustment circuit connected to the amplifier circuit and adjusting an amplification multiple of the amplifier circuit.

4. The transformer according to claim 3, further comprising an alarm unit connected to the three-terminal synchronization rectifier and driving the alarm unit to generate an alarm if an induction value output by the current induction device exceeds a preset value.

5. The transformer according to claim 1, further comprising a control winding current induction device, a standby controller and a standby control winding, the control winding current induction device being provided in the circuit of the control winding and detecting an induction current value of the control winding; the input end of the standby controller being connected to the output end of the current induction device and the output end of the control winding current induction device respectively, the output end of the standby controller being connected to the standby control winding, wherein the standby control winding starts up to operate when it is detected that the matching value of the induction current in the load line and the current value of the control winding goes beyond a preset matching interval; and the standby control winding being provided in the winding of the second transformer.

6. The transformer according to claim 5, further comprising a control winding cutoff switch provided in the line of the control winding, connected to the output end of the standby controller and being cut off when the standby controller drives the standby control winding to start up.

7. A transformer comprising:
a first transformer;
a second transformer; a current induction device; and
an amplifier circuit,
wherein the current induction device is provided in a load line of the first transformer for detecting an induction current in the load line of the first transformer;
wherein an induction output end of the current induction device is connected to a control winding and the control winding is provided in a winding of the second transformer for generating an induction voltage in the winding of the second transformer so as to supplement the output power of the first transformer;
wherein the amplifier circuit is provided in an induction output line of the current induction device;
wherein the amplifier circuit protects a first amplifier circuit and a second amplifier circuit; and
wherein the first amplifier circuit has a first amplification coefficient value and the second amplifier circuit has a second amplification coefficient value.

8. The transformer according to claim 7, further comprising a humidity sensor and an amplification switching adjustment controller, the humidity sensor being provided in the load line for detecting an environment humidity value of the load line, the induction output end thereof being connected to the input end of the amplification switching adjustment controller, and the output end of the amplification switching adjustment controller being connected to the first amplifier circuit and the second amplifier circuit for making a switch from the first amplifier circuit to the second amplifier circuit if the environment humidity value exceeds a preset value.

9. The transformer according to claim 7, further comprising an over-range adjustment circuit connected to the amplifier circuit and adjusting an amplification multiple of the amplifier circuit.

10. The transformer according to claim 9, further comprising an alarm unit connected to the three-terminal synchronization rectifier and driving the alarm unit to generate an alarm if an induction value output by the current induction device exceeds a preset value.

11. The transformer according to claim 7, further comprising a control winding current induction device, a standby controller and a standby control winding, the control winding current induction device being provided in the circuit of the control winding and detecting an induction current value of the control winding; the input end of the standby controller being connected to the output end of the current induction device and the output end of the control winding current induction device respectively, the output end of the standby controller being connected to the standby control winding, wherein the standby control winding starts up to operate when it is detected that the matching value of the induction current in the load line and the current value of the control winding goes beyond a preset matching interval; and the standby control winding being provided in the winding of the second transformer.

12. The transformer according to claim 11, further comprising a control winding cutoff switch provided in the line of the control winding, connected to the output end of the standby controller and being cut off when the standby controller drives the standby control winding to start up.

* * * * *